United States Patent [19]

Arnold et al.

[11] 4,200,789
[45] Apr. 29, 1980

[54] MEASURING OIL AND WATER CUTS IN A MULTIPHASE FLOWSTREAM WITH ELIMINATION OF THE EFFECTS OF GAS IN DETERMINING THE LIQUID CUTS

[75] Inventors: Dan M. Arnold; Harry D. Smith, Jr., both of Houston, Tex.

[73] Assignee: Texaco Inc., White Plains, N.Y.

[21] Appl. No.: 920,568

[22] Filed: Jun. 29, 1978

[51] Int. Cl.² .................. G01V 5/00; G01N 23/00
[52] U.S. Cl. .................................. 250/270; 250/359
[58] Field of Search ............ 250/269, 270, 301, 356, 250/358, 359, 360, 435

[56] References Cited

U.S. PATENT DOCUMENTS

| | | | |
|---|---|---|---|
| 3,240,938 | 3/1966 | Hall, Jr. | 250/270 |
| 3,263,082 | 7/1966 | Caldwell | 250/269 |
| 3,521,064 | 7/1970 | Moran et al. | 250/269 |

Primary Examiner—Davis L. Willis
Assistant Examiner—Janice A. Howell
Attorney, Agent, or Firm—Carl G. Ries; Thomas H. Whaley; William J. Beard

[57] ABSTRACT

In a pipeline or container at any of various petroleum producing operations, a multiphase fluid flowstream containing oil, water and gas is bombarded with neutrons and high energy gamma rays resulting from capture of thermal neutrons are detected. The spectra of the detected gamma rays are then analyzed to determine the ratio of the gamma ray counts of the element sulfur to the element chlorine. From this ratio, the oil and water cuts of the fluid may be measured while eliminating the effects of gas in the flowstream on the measurements.

22 Claims, 5 Drawing Figures

MEASURING OIL AND WATER CUTS IN A MULTIPHASE FLOWSTREAM WITH ELIMINATION OF THE EFFECTS OF GAS IN DETERMINING THE LIQUID CUTS

CROSS-REFERENCE TO RELATED APPLICATIONS

The present application is an improvement on the subject matter of United States Patent Application Ser. No. 748,072, filed Dec. 6, 1976, and assigned to the assignee of the present invention but now abandoned.

BACKGROUND OF THE INVENTION

1. Field of Invention:

The present invention relates to nuclear techniques for measuring oil and water cuts in a multiphase flowstream in petroleum refining and producing operations.

2. Description of Prior Art:

U.S. Patent Application Ser. No. 748,072 relates to a new and improved method and apparatus for determining the presence of salt water in a fluid conduit, such as crude oil at a wellhead, loading dock or other location, or refined product, feed stock or waste water to dispose of at a refinery.

With this technique, the fluid is bombarded with fast neutrons from a neutron source which are slowed down and thereafter engage in thermal neutron capture reactions with materials in the fluid, giving rise to thermal neutron capture gamma rays. The energy spectra of the thermal neutron capture gamma rays are obtained, from which a measure of the relative pressence of chlorine in the fluid may be ascertained, so that if the salinity of the fluid is known, the relative presence of salt water can accordingly be determined. Further, the relative pressure of sulfur may be determined simultaneously with the relative presence of chlorine.

In certain applications, however, it has been found that this technique has limits. For example, it has been found that where the water cut becomes significant, the difference in hydrogen index between the two liquid phases is no longer small relative to that between the gas and liquids, introducing errors in hydrogen normalization. Additionally, if chlorine concentrations increase above very low levels, degraded chlorine gamma rays interfere with gamma ray counts in the hydrogen energy window, and decrease the accuracy of the measurements obtained.

SUMMARY OF INVENTION:

Briefly, the present invention relates to a new and improved method and apparatus for determining the water cut of a multiphase fluid flowstream containing oil, water and gas. The flowstream is in a conduit and may be at a wellhead, loading dock or my be feed stock in a refinery or other location.

The fluid is bombarded with fast neutrons from a neutron source which are slowed down and thereafter engage in thermal neutron capture reactions with materials in the fluid, giving rise to thermal neutron capture gamma rays. The energy spectra of the thermal neutron capture gamma rays are obtained from which a measure of the concentration of chlorine and a measure of the concentration of sulfur in the fluid are determined. Where the salinity of water in the fluid and the sulfur content of the oil in the fluid are known, the water cut and the oil cut of the fluid can accordingly be determined.

Figure 1:
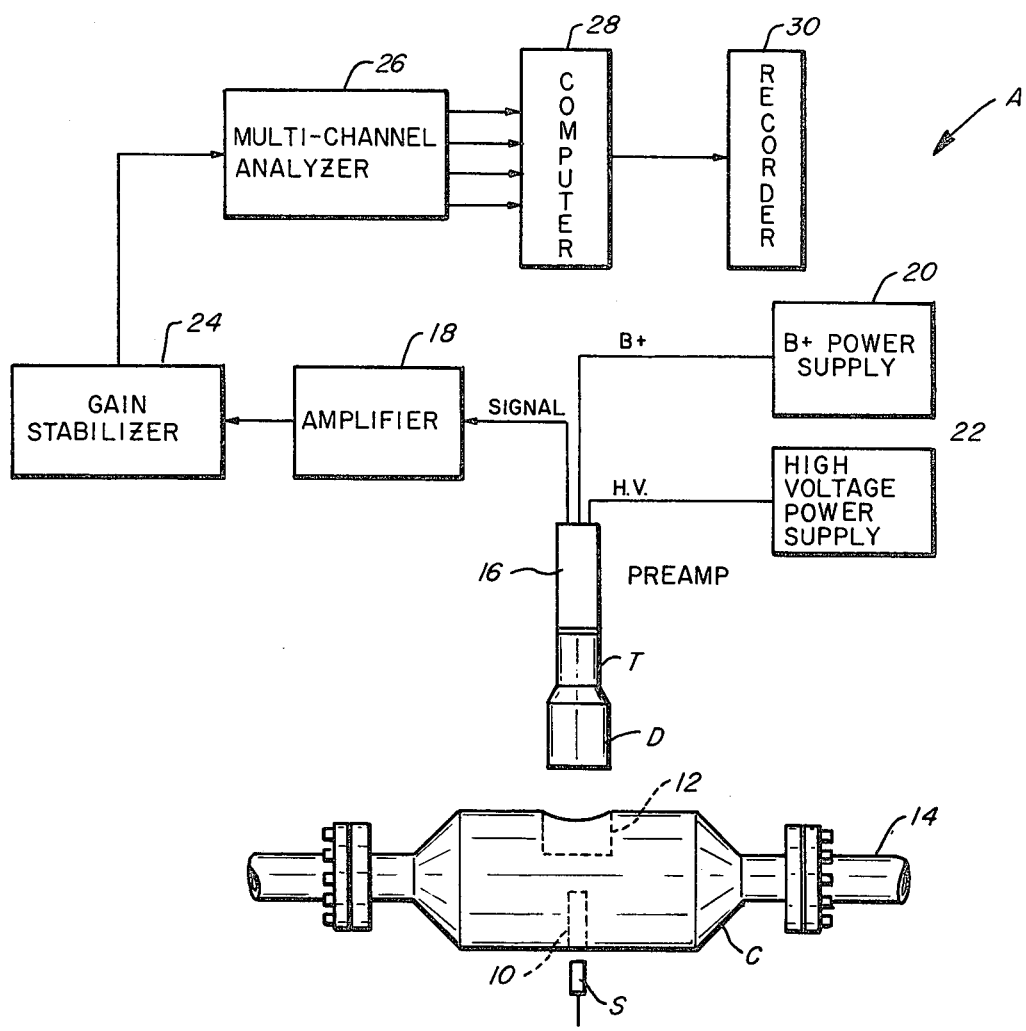
FIGS. 1 and 2 are schematic block diagrams of apparatus according to the present invention.

DESCRIPTION OF THE PREFERRED EMBODIMENT:

FIG. 1 shows an apparatus A according to the present invention with a neutron source S and a detector D mounted in suitable sockets 10 and 12, respectively, of a counting chamber C mounted in a crude oil flow line 14. The detector D is preferably a 5"×5" NaI(Tl) cylindrical crystal coupled to a photomultipler tube T. The source S shown is a $Cf^{252}$ neutron source emitting $5 \times 10^7$ neutrons per second, although it should be understood that a different source material such as actinium-beryllium, americium-boron or americium-beryllium could be used, if desired.

The chamber C preferably should be constructed of some material which contains no elements producing appreciable capture gamma radiation above 5.0 MeV. Aluminum or certain fiberglass-epoxy materials would be suitable, although iron, which produces 9.30 and 7.64 MeV gamma radiation through (n,γ) reactions, should be avoided. It should be noted that the chamber C is designed such that the detector D and source S are physically isolated in the sockets 10 and 12 from the crude oil. This eliminates the possibility of contaminating the crude oil if the source S should leak and also permits the detector D and source S to be removed without interrupting the flow of crude oil.

Figure 2:
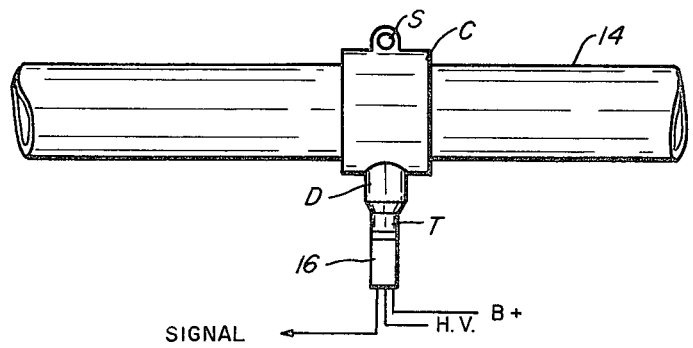

The physical shape of the chamber C is not critical as long as the source S and detector D are surrounded by at least several inches of liquid. FIG. 2 depicts an alternate configuration wherein the source S and detector D are mounted external to the flowline 14. In certain situations it might be desirable to coat the inside of the chamber C with a durable material of high thermal neutron cross capture cross section, such as boron. This is especially true if iron cannot be eliminated in the fabrication of the chamber. This material would reduce the thermal neutron interactions with the walls of the chamber and also prevent the escape from the chamber of thermal neutrons that might react with elements outside the chamber producing additional "background" radiation. Boron (boron carbide mixed with epoxy resin) would be ideal for this application since it has a large thermal neutron capture cross section ($\sigma = 775$ barns) and a capture reaction which produces no radiation above 5.0 MeV.

The detector D produces scintillations or discrete flashes of light whenever gamma rays pass therethrough, while the photomultiplier tube T generates in response to each such scintillation a voltage pulse proportional to the intensity of the scintillation. A conventional preamplifier circuit 16 amplifies the pulses from the photomultiplier tube T and furnishes the amplifier pulses to a further amplifier stage 18. A $B^+$ power supply 20 is provided for the preamplifier 16, and a high voltage power supply 22 is provided for the photomultiplier tube T.

Figure 3:
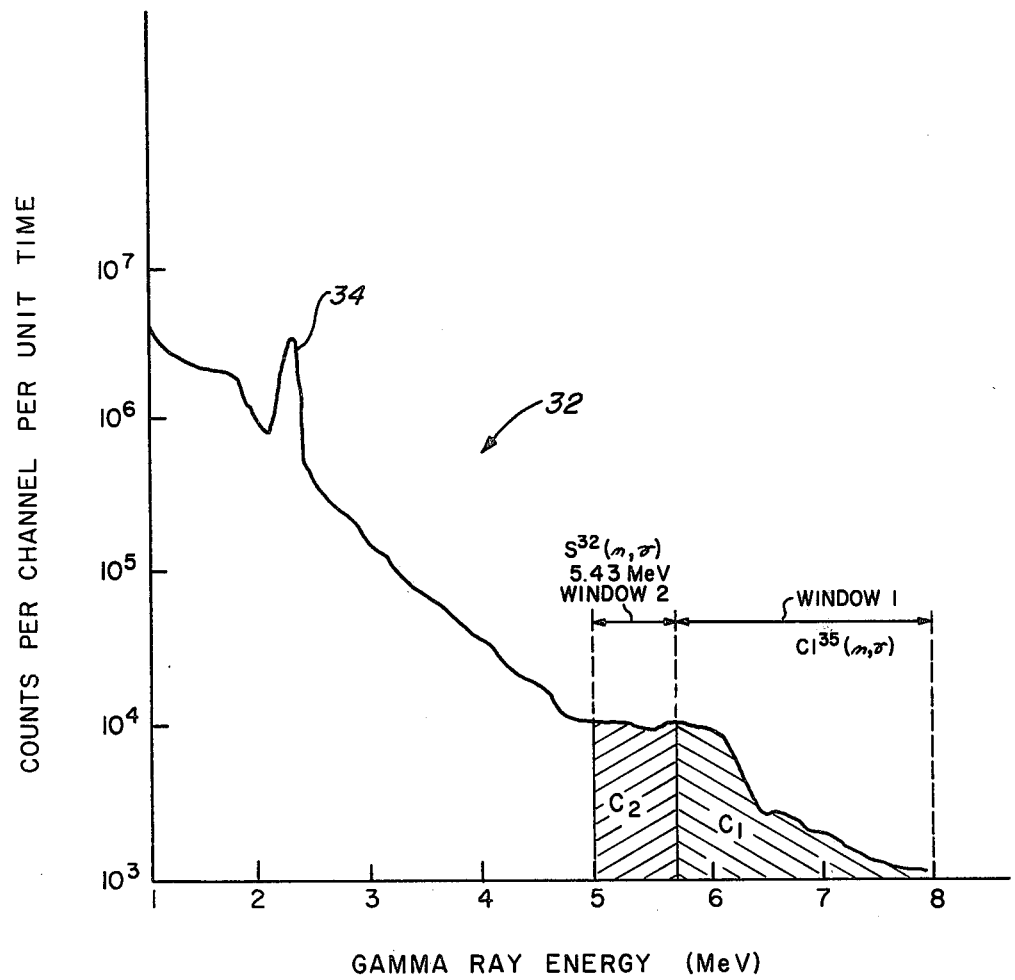
FIG. 3 is a graphical illustration of a typical thermal neutron capture gamma ray spectrum for crude oil.

The output pulses from the amplifier 18 are furnished to a gain stabilizer circuit 24 which is calibrated to respond to the energy level of a selected reference peak in the gamma ray energy spectrum, such as the pronounced 2.23 MeV energy peak of hydrogen 34 (FIG. 3). It should be understood, however, that other gamma ray energy peaks, a peak generated from the output of a light emitting diode positioned within the detector crystal D, or a mercury pulser may be used for gain stabilization, if desired. The gain stabilizer circuit 24 is an automatic gain control circuit which responds to energy level of pulses at the calibrated peak level and adjusts the gain of all energy level pulses to compensate for gain shift or variations in tube T and other circuitry of the apparatus of the present invention due to power supply voltage fluctuations and/or temperature effects.

The output pulses from gain stabilizer circuit 24 are supplied to a pulse height or multi-channel analyzer 26. The pulse height analyzer 26 may be of conventional design as known in the art and having, for example, two or more channels or energy divisions corresponding to quantizations or energy ranges of the pulse heights of the input pulses, if desired. The pulse height analyzer 26 functions to sort and accumulate a running total of the incoming pulses into a plurality of storage locations or channels based on the height of the incoming pulses which, it will be recalled, is directly related to the energy of the gamma rays causing the pulse. The output of the pulse height analyzer 26 in the case of the present invention consists of count pulses occurring in each of two energy ranges or windows as depicted in FIG. 3. It should also be understood that two appropriately biased single channel analyzers may be used in place of the multichannel analyzer 26, if desired.

The output from the pulse height analyzer 26 may be stored on a suitable memory device for subsequent processing, or alternatively, is supplied directly over an appropriate number of lines to a computer 28, which obtains from the number of chlorine counts, the sulfur counts and the length of time for such counts, the water cut of the fluid in the line 14, in a manner to be set forth. Further, the computer 28 may also determine from the output of analyzer 26 the oil cut of the fluid in line 14. The results of such computations may be stored or displayed, as desired with a recorder 30 or other suitable display device.

FIG. 3 shows a typical capture gamma ray spectrum 32 recorded using the equipment of FIG. 1 for a stream of crude oil containing small amounts of clorine and sulfur. The intense peak of 2.23 MeV of hydrogen indicated by reference numeral 34 results from the capture of thermal neutrons by hydrogen in the crude oil and may be used, as set forth above, as an energy reference peak by the gain stabilizer circuit of FIG. 1. FIG. 3 also shows the energy settings of the multi-channel analyzer 26. The first setting, identified as "Window 1", extends from 5.75 to 8.0 MeV and includes photoelectric and escape peaks from the 7.79, 7.42, 6.64 and 6.11 MeV radiation from the $Cl^{35}$ $(n,\gamma)$ $Cl^{36}$ reaction as well as the less intense 7.78, 7.42, 7.19, 6.64 and 5.97 MeV peaks from sulfur. The second setting, identified as "Window 2", extends from 5.00 to 5.75 MeV and includes the relatively intense 5.42 MeV sulfur capture peak.

Relatively small concentrations of salt water in crude oil can often cause major problems in the crude oil refining process. The present invention relates to the detection in a flowing multiphase fluid crude oil stream, or other petroleum conduit, of the water cut and oil cut of the fluid while eliminating the effects of gas, such as free gas, in the fluid on the determination of water cut and oil cut. The present invention is based upon the bombardment or irradiation of a flowing stream of crude oil with neutrons and the detection of gamma radiation emitted by the elements chlorine and sulfur upon capture of thermal neutrons. For a given thermal neutron flux, the yield of chlorine capture radiation has been found to be proportional to the water cut of the fluid, while the yield of sulfur capture radiation is proportional to the oil cut. However, determination of the oil cut and water cut is not a routine computation from the chlorine and sulfur radiation yields. First, the radiation peaks of sulfur and chlorine overlap somewhat in the gamma ray spectrum. Also, if the water cut of the fluid becomes significant, the assumption that the difference between hydrogen indices in the water and oil phases of the flowstream are small relative to the gas phase introduces errors in hydrogen normalization.

Gamma radiation resulting from thermal capture $(n,\gamma)$ reactions is "prompt" in the sense that it is emitted within microseconds after the capture event. This is in contrast to "delayed" gamma radiation resulting from "activation" type reactions which is emitted from milliseconds to years after the reaction. Since thermal neutron capture capture radiation is almost instantaneous, the velocity and volume flow rate of the crude oil stream do not affect the measurement. Another advantage of the present invention is that since thermal neutrons are required, a chemical source rather than an evacuated envelope accelerator type neutron generator source can be used. Chemical sources are relatively inexpensive and, of course, require no associated electronics or maintenance.

For a fixed count time T, an expression for the observed chlorine window count rate, $W_{CL}$, in Window 1 (FIG. 3) is given by:

$$W_{CL} = G(P_G) \cdot C_{CL} + G(P_G) \cdot C_{CLB} \tag{1}$$

where:
$G(P_G) \cdot C_{CL}$ = chlorine counts in $W_{CL}$
$G(P_G) \cdot C_{CLB}$ = non-chlorine counts in $W_{CL}$
$G(P_G)$ = gas scale factor related to the gas fraction $P_G$ in flowline where $G(0) = 1.0$ and $G(1) = 0.0$.

A similar expression can be obtained for sulfur window count rate, $W_S$, in Window 2 for the count time T which also includes a degraded chlorine component:

$$W_S = G(P_G) \cdot C_S + G(P_G) \cdot C_{SB} + G(P_G) \cdot K \cdot C_{CL} \tag{2}$$

where:
$G(P_G) \cdot C_S$ = sulfur counts in $W_S$
$G(P_G) \cdot C_{SB}$ = non-sulfur and non-chlorine counts in $W_S$
$G(P_G) \cdot K \cdot C_{CL}$ ≡ chlorine counts in $W_S$
K ≡ geometrical constant
$G(P_G)$ ≡ as defined above
The ratio R of these count rates is given by:

$$R \equiv W_S / W_{CL} = (C_S + C_{SB} + K \cdot C_{CL}) / (C_{CL} + C_{CLB}) \tag{3}$$

It is to be noted that the ratio R cancels the gas scale factor $G(P_G)$. The count rates $C_{SB}$ and $C_{CLB}$ and constant K in Equation (3) are calibration constants based on source-detector spacing, source strength, detector size and the like and are thus independent of the water cut, $L_{WC}$, in the liquid flow phase. $C_S$ in Equation (3) is proportional to the sulfur content of the liquid phase of the flowstream. For a producing formation, the sulfur concentration $P_S$ in the oil phase is substantially constant and can be accurately determined. Also, in formations which are not being subjected to water or steam flooding, the salinity $P_{Cl}$ of the formation water stays substantially constant and can also be accurately determined independently from a sample of produced water. With the present invention, it has been found that these known factors together with the sulfur and chlorine counts from the pulse height analyzer 26 may be used to accurately determine the oil and water cut of a multi-phase fluid flowstream while eliminating the effects of gas in the flowstream on the measurements.

For liquid phases with salinity $P_{CL}L_{WC}$ less than about 60,000 ppm chlorine, hydrogen-chlorine neutron capture competition is negligible. Assuming that all chlorine contained in the liquid phase is contained in the water phase, the counts for chlorine can thus be expressed as $$C_{CL} = \beta P_{CL} L_{WC} \tag{4}$$

where $\beta$ is a geometrically related calibration constant.

Likewise, assuming that all sulfur contained in the liquid phase is contained in the oil phase, the counts $C_S$ for chlorine can be expressed as:

$$C_S = \alpha P_S (1 - L_{WC}) \tag{5}$$

where $\alpha$ is also a calibration constant determined by the geometry of the system.

Substituting Equations (4) and (5) into (3) yields:

$$R = [\alpha P_S(1 - L_{WC}) + C_{SB} + K P_{CL} \beta L_{WC}] \div [P_{CL} \beta L_{WC} + C_{CLB}] \tag{6}$$

where $\alpha$, $\beta$, K, $C_{SB}$ and $C_{CLB}$ are known calibration constants and the sulfur content $P_S$ and salinity $P_{CL}$ are known values for the flowstream. The value of the measured ratio R is obtained from the measured gamma radiation counts $W_S$ and $W_{CL}$, so that the oil cut, $1-L_{WC}$, and the water cut, $L_{WC}$, of the flowstream may be readily determined.

To consider a specific example, for a 24" diameter chamber C and a source S and detector D of the type set forth above, the following constants were obtained:

$$C_{SB} = 2760 \text{ cpm}$$

$$C_{CLB} = 3645 \text{ cpm}$$

$$K = 0.73 \tag{7}$$

$\alpha = 555$ cpm per % sulfur
$\beta = 5.87$ cpm per ppm chlorine, using a chlorine window of 5.75–8.00 MeV and a sulfur window of 5.00–5.75 MeV.

Figure 4:
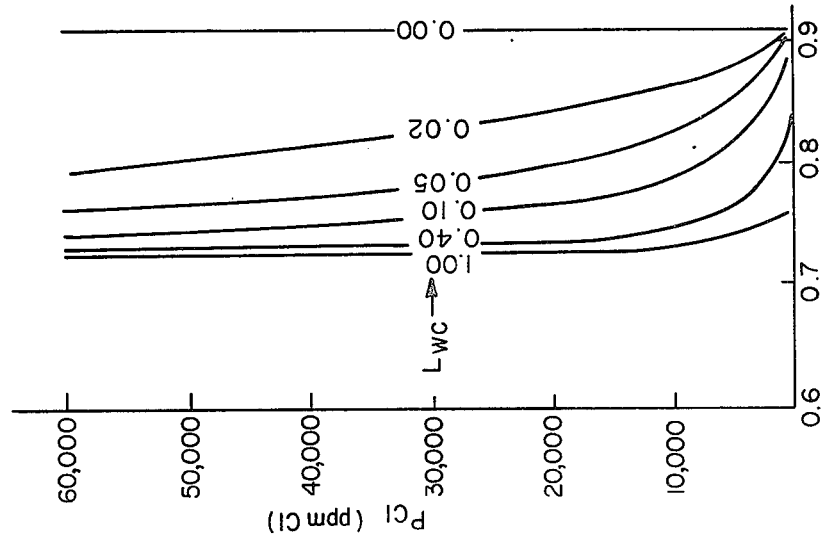

FIG. 4 shows a plot of the measured ratio, R, from Equation (3) (using constants from Equations (7)) versus water salinity $P_{CL}$ according to the present invention for various water cuts $L_{WC}$ and a sulfur concentration of 1% ($=P_S$). Examining FIG. 1, it can be seen that $L_{WC}$ can be determined with reasonable accuracy if the water salinity is known and the product $L_{WC} \cdot P_{CL} \lesssim 6{,}000$.

Figure 5:
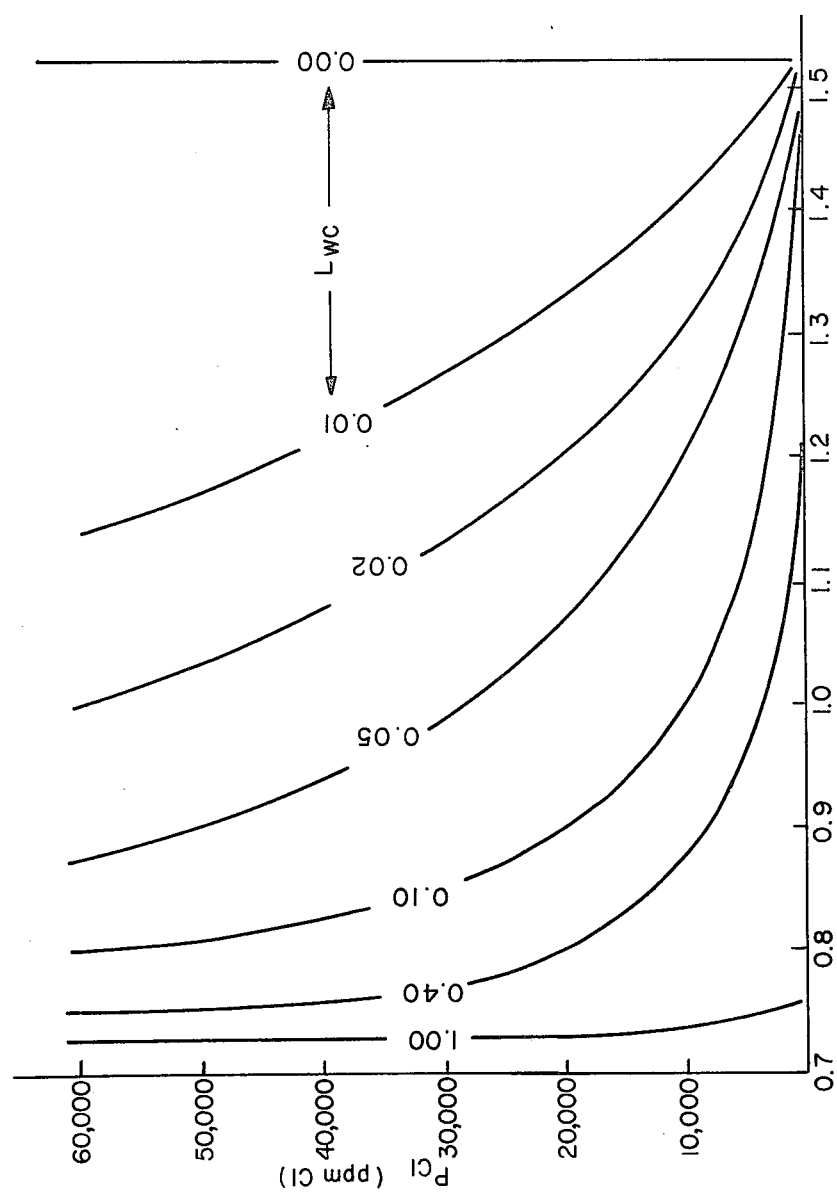
FIGS. 4 and 5 are graphical illustrations of the measured ratio of sulfur neutron capture gamma ray count to chlorine neutron capture gamma ray count versus water salinity for various water cuts and sulfur concentrations in a fluid in accordance with the present invention.

FIG. 5 again shows a plot of R versus $P_{CL}$ according to the present invention but for an oil containing 5% sulfur. It is apparent that as the sulfur content of the oil increases, the range of salinities and water cuts over which $L_{WC}$ can be measured also increases. At $P_S = 5\%$, $L_{WC}$ can be determined with reasonable accuracy for $L_{WC} \cdot P_{CL} \lesssim 24{,}000$.

The foregoing disclosure and description of the invention are illustrative and explanatory thereof, and various changes in the size, shape and materials, as well as in the details of the illustrated construction may be made without departing from the spirit of the invention.

We claim:

1. A method for analysis of a fluid containing liquid and gas and flowing in a conduit to determine the water and oil cuts of the fluid, comprising the steps of:
   (a) bombarding the fluid with fast neutrons which are slowed down and thereafter engage in thermal neutron capture reactions with materials in the fluid;
   (b) obtaining gamma ray energy spectra of the materials in response to the capture of thermal neutrons by the materials in the fluid;
   (c) obtaining a measure of the concentration of chlorine in the fluid from the gamma ray energy spectra;
   (d) obtaining a measure of the concentration of sulfur in the fluid from the gamma ray energy spectra; and
   (e) obtaining from a ratio of the concentration of sulfur to the concentration of chlorine the water and oil cuts of the fluid.

2. The method of claim 1, wherein the fluid is feed stock in a petroleum refining conduit.

3. The method of claim 1, wherein the fluid is observed in a wellhead conduit at an oil well.

4. The method of claim 1, wherein the fluid is observed at a loading dock.

5. The method of claim 1, wherein the fluid is waste fluid which is to be disposed.

6. The method of claim 1, wherein said step of obtaining gamma ray energy spectra includes:
   obtaining gamma rays from sulfur in the range of from 5.0 MeV to 5.75 MeV.

7. The method of claim 1, wherein said step of obtaining gamma ray energy spectra includes:
   obtaining gamma rays from chlorine in the range of from 5.75 MeV to 8.0 MeV.

8. The method of claim 1, wherein said fast neutrons are emitted from a neutron source and further including the step of:
   attaching said neutron source to the conduit prior to said step of bombarding.

9. The method of claim 1, wherein said fast neutrons are emitted from a neutron source and further including the step of:
   inserting said neutron source into the conduit prior to said step of bombarding.

10. The method of claim 1, wherein said gamma ray spectra are obtained in a detector and further including the step of:
    inserting said detector into the conduit.

11. The method of claim 1, wherein said gamma ray spectra are obtained in a detector and further including the step of:
    attaching said detector to the conduit.

12. An apparatus for analysis of a fluid containing liquid and gas and flowing in a conduit to determine the water cut of the fluid, comprising:
   (a) means for bombarding the fluid with fast neutrons, which are slowed down and thereafter engage in thermal neutron capture reactions with materials in the fluid;
   (b) means for obtaining gamma ray energy spectra of the materials in response to the capture of thermal neutrons by the materials in the fluid;
   (c) means for obtaining a measure of the concentration of chlorine in the fluid from the gamma ray energy spectra;
   (d) means for obtaining a measure of the concentration of sulfur in the fluid from the gamma ray energy spectra; and
   (e) means for obtaining from a ratio of the concentration of sulfur to the concentration of chlorine the water and oil cuts of the fluid.

13. The apparatus of claim 12, wherein said means for bombarding is mounted adjacent a petroleum refining conduit to bombard refinery feed stock and sense the presence of salt water and oil in feed stock in said conduit.

14. The apparatus of claim 12, wherein said means for bombarding is mounted adjacent a well head conduit at an oil well to bombard well fluid with neutrons to sense the presence of salt water and oil in the produced fluid.

15. The apparatus of claim 12, wherein said means for bombarding is mounted adjacent a conduit at a loading dock to bombard the flowstream with neutrons to sense the presence of salt water and oil in the flowstream.

16. The apparatus of claim 12, wherein said means for bombarding is mounted adjacent a conduit to bombard with neutrons waste fluid to be disposed to sense the presence of salt water and oil therein.

17. The apparatus of claim 12, wherein said means for obtaining includes:
   means for obtaining gamma rays from sulfur in the range of from 5.0 MeV to 5.75 MeV.

18. The apparatus of claim 12, wherein said means for obtaining includes:
   means for obtaining gamma rays from chlorine in the range of from 5.75 MeV to 8.0 MeV.

19. The apparatus of claim 12, wherein said means for bombarding is attached to the exterior of said conduit.

20. The apparatus of claim 12, wherein said means for bombarding is inserted into the exterior of said conduit.

21. The apparatus of claim 12, wherein said means for obtaining gamma ray spectra is attached to the exterior of said conduit.

22. The apparatus of claim 12, wherein said means for obtaining gamma ray spectra is inserted into the exterior of said conduit.

* * * * *